United States Patent
Katayama et al.

(10) Patent No.: US 7,329,855 B2
(45) Date of Patent: Feb. 12, 2008

(54) OPTICAL INSPECTION OF GLASS BOTTLES USING MULTIPLE CAMERAS

(75) Inventors: Kaoru Katayama, Yokohama (JP); Toru Ishikura, Yokohama (JP); Yasusaburo Kodama, Yokohama (JP); Hiroyuki Fukuchi, Yokohama (JP); Akira Fujiwara, Soka (JP)

(73) Assignee: Kirin Techno-System Corporation, Kanagawa (JP)

(*) Notice: Subject to any disclaimer, the term of this patent is extended or adjusted under 35 U.S.C. 154(b) by 0 days.

(21) Appl. No.: 10/531,521

(22) PCT Filed: Oct. 18, 2002

(86) PCT No.: PCT/JP02/10838

§ 371 (c)(1),
(2), (4) Date: Apr. 15, 2005

(87) PCT Pub. No.: WO2004/036197

PCT Pub. Date: Apr. 29, 2004

(65) Prior Publication Data

US 2006/0000968 A1    Jan. 5, 2006

(51) Int. Cl.
B07C 5/12    (2006.01)
G01N 21/00    (2006.01)
G01N 21/90    (2006.01)

(52) U.S. Cl. .............................. 250/223 B; 356/239.4; 356/428

(58) Field of Classification Search ............ 250/223 B; 356/239.4, 428, 142; 382/142

See application file for complete search history.

(56) References Cited

U.S. PATENT DOCUMENTS 4,244,650 A * 1/1981 Garfunkel et al. ............ 356/71
4,758,084 A * 7/1988 Tokumi et al. .......... 356/239.4
4,872,757 A * 10/1989 Cormack et al. ........... 356/612

(Continued)

FOREIGN PATENT DOCUMENTS

EP    0952443 A1    10/1999

(Continued)

OTHER PUBLICATIONS

Patent Abstracts of Japan for JP63-277960 published on Nov. 15, 1988.

(Continued)

*Primary Examiner*—Thanh X. Luu
(74) *Attorney, Agent, or Firm*—Darby & Darby P.C.

(57) ABSTRACT

A glass bottle inspecting apparatus is presented which can detect a defect at a specific location of a bottle-mouth portion of a glass bottle. An inspecting apparatus detects a defect of a glass bottle by imaging light from the glass bottle while the glass bottle (2) is illuminated and rotated, and processes the obtained image. A glass bottle inspecting apparatus includes a lighting device (7) disposed at a pre-determined position with respect to the glass bottle, a plurality of CCD cameras (11-20) disposed around the glass bottle for imaging a specific part of the glass bottle, an angle detection device (10) for detecting a rotation angle of the glass bottle with respect to a reference position, and an image processor (8) for processing the images obtained by the CCD cameras. The image processor stores rotation angle information detected by the angle detection device in such a manner that the rotation angle information corresponds to the image imaged by each of the CCD cameras.

9 Claims, 16 Drawing Sheets

U.S. PATENT DOCUMENTS

| | | | |
|---|---|---|---|
| 5,405,015 A | | 4/1995 | Bhatia et al. |
| 5,969,810 A | * | 10/1999 | Nicks et al. ............. 356/239.4 |
| 6,104,482 A | | 8/2000 | Brower et al. |
| 6,134,343 A | | 10/2000 | Nichani |

FOREIGN PATENT DOCUMENTS

| | | |
|---|---|---|
| JP | 63-277960 A | 11/1988 |
| JP | 04-294262 A1 | 10/1992 |
| JP | 09-119902 A1 | 5/1997 |
| JP | 10-082624 A1 | 3/1998 |
| JP | 10-157798 A | 6/1998 |
| JP | 10-160430 A1 | 6/1998 |
| JP | 2000-214104 A1 | 8/2000 |
| JP | 2001-221748 A | 8/2001 |

OTHER PUBLICATIONS

Patent Abstracts of Japan for JP10-157798 published on Jun. 16, 1998.

Patent Abstracts of Japan for JP2001-221748 published on Aug. 17, 2001.

International Search Report for PCT/JP02/10838 mailed Jan. 14, 2003.

* cited by examiner

F I G. 2
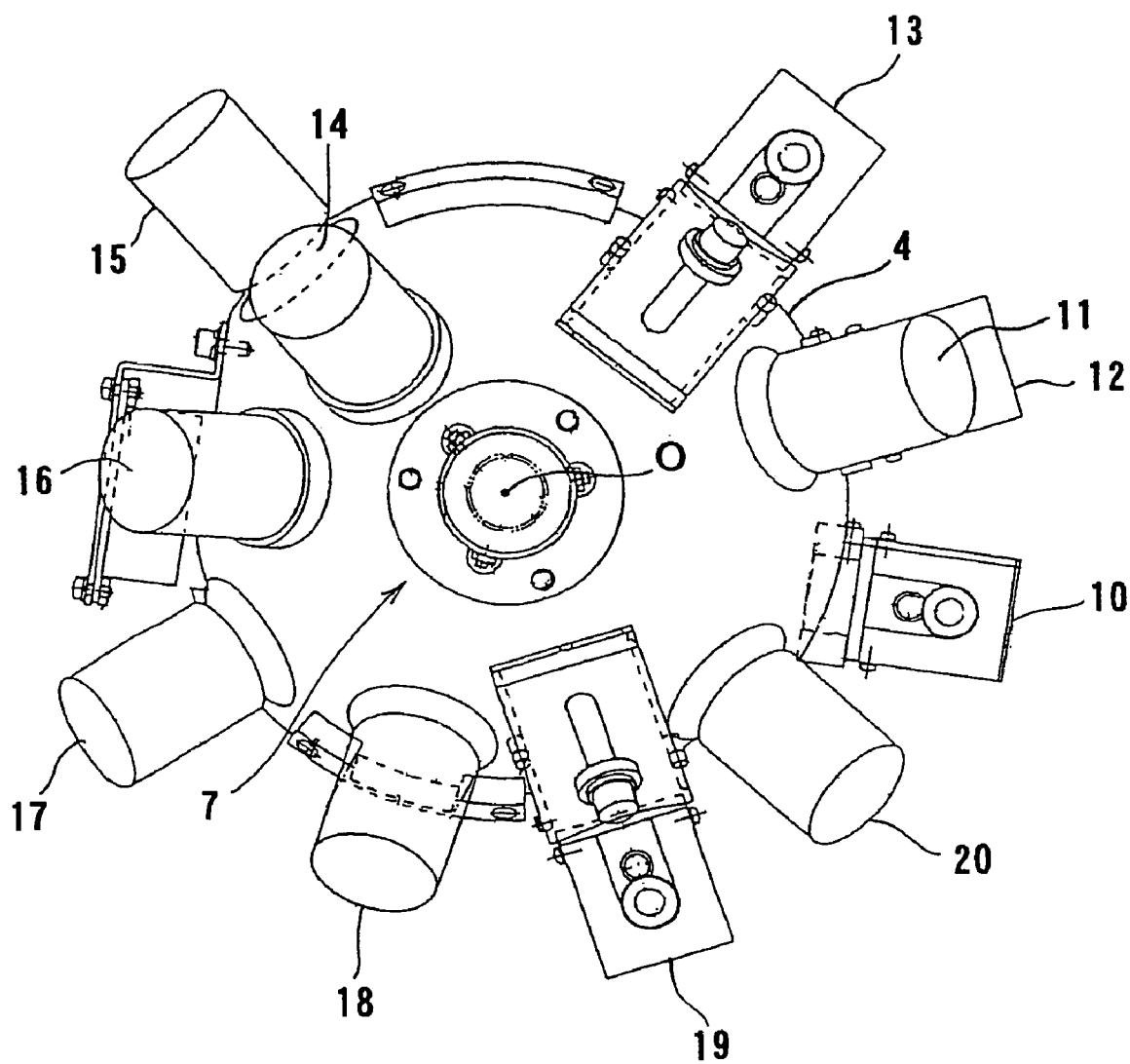

F I G. 5
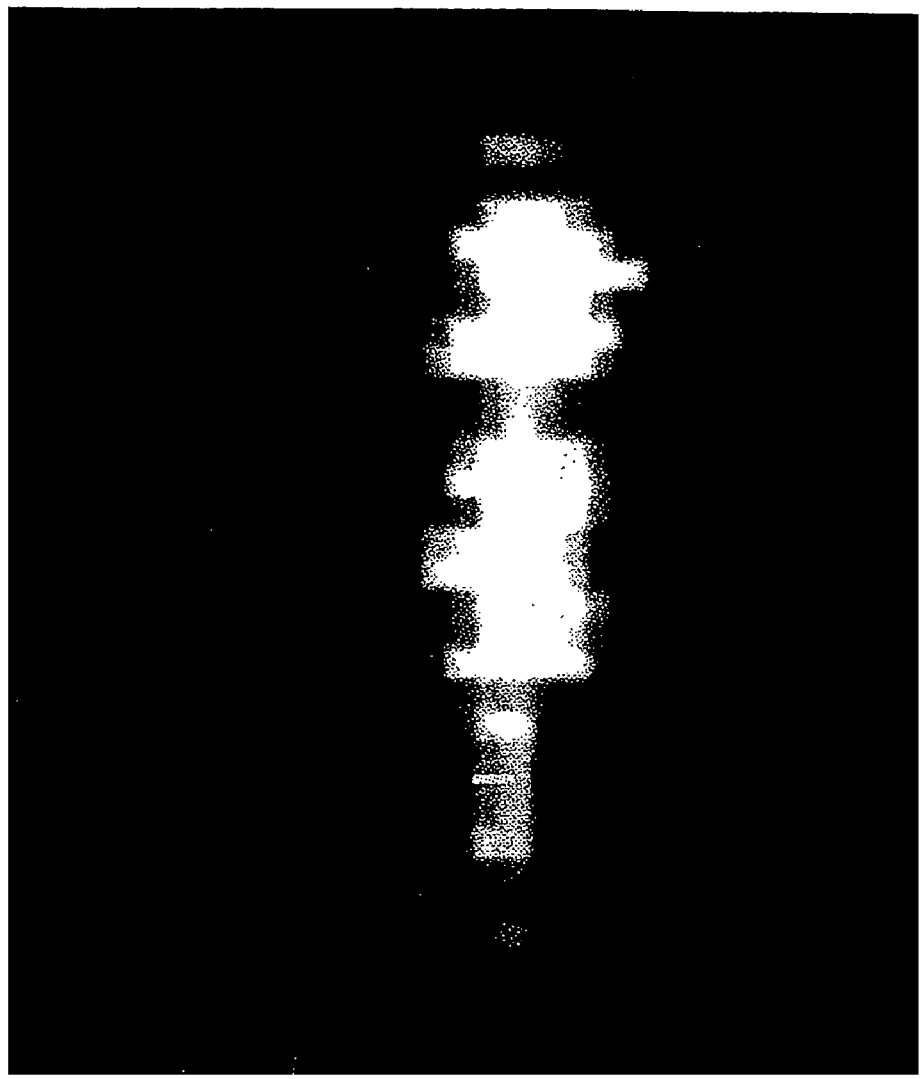

F I G. 6
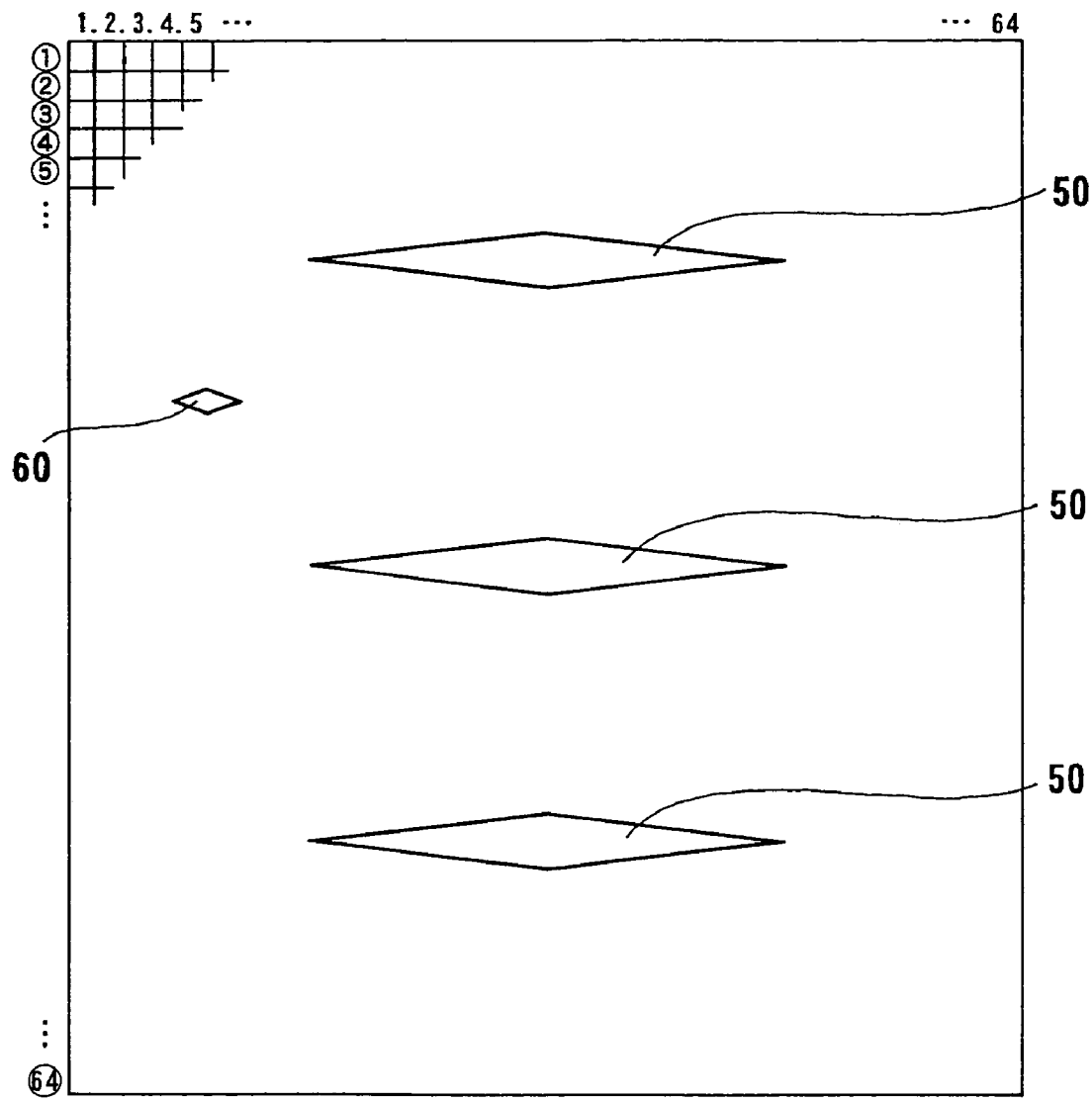

FIG. 11A

|   | 1 | 2 | 3 | 4 | 5 | ... | m | ... | | 64 |
|---|---|---|---|---|---|---|---|---|---|---|
| 1 | 0A | 0A | 0A | 02 | 04 | | | | | |
| 2 | 0A | 0A | 0A | 04 | 04 | | | | | |
| 3 | 05 | 05 | 05 | 03 | | | | | | |
| 4 | 07 | 07 | 05 | | | | | | | |
| 5 | 0B | 0B | | | | | | | | |
| ... | | | | | | | | | | |
| n | 0B | 0B | 0A | 07 | 06 | 06 ... | 08 | ... | 07 | 08 | 08 |
| ... | | | | | | | | | | |
| 64 | | | | | | | | | | |

FIG. 11B

|   | 1 | 2 | 3 | 4 | 5 | ... | m | ... | | 64 |
|---|---|---|---|---|---|---|---|---|---|---|
| 1 | 02 | 00 | 00 | 00 | 00 | | | | | |
| 2 | 00 | 00 | 00 | 00 | 00 | | | | | |
| 3 | 00 | 00 | 00 | 00 | | | | | | |
| 4 | 00 | 00 | 00 | | | | | | | |
| 5 | 00 | 00 | | | | | | | | |
| ... | | | | | | | | | | |
| n | 04 | 04 | 00 | 00 | 02 | 02 ... | 02 | ... | 00 | 00 | 00 |
| ... | | | | | | | | | | |
| 64 | | | | | | | | | | |

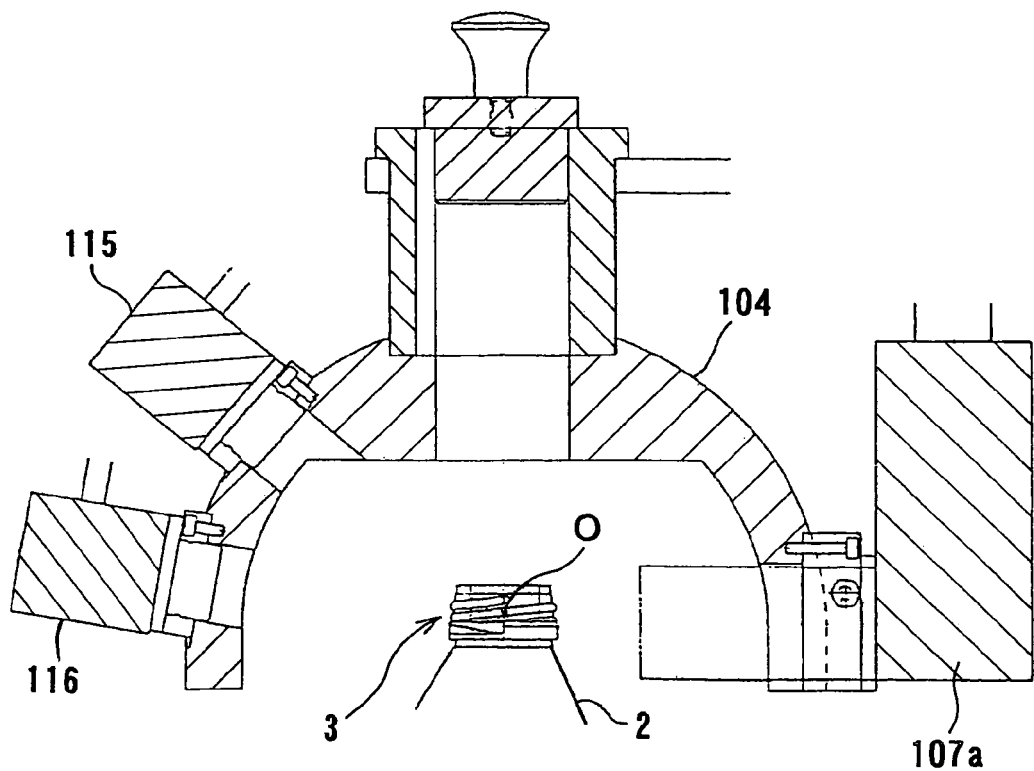
F I G. 1 4

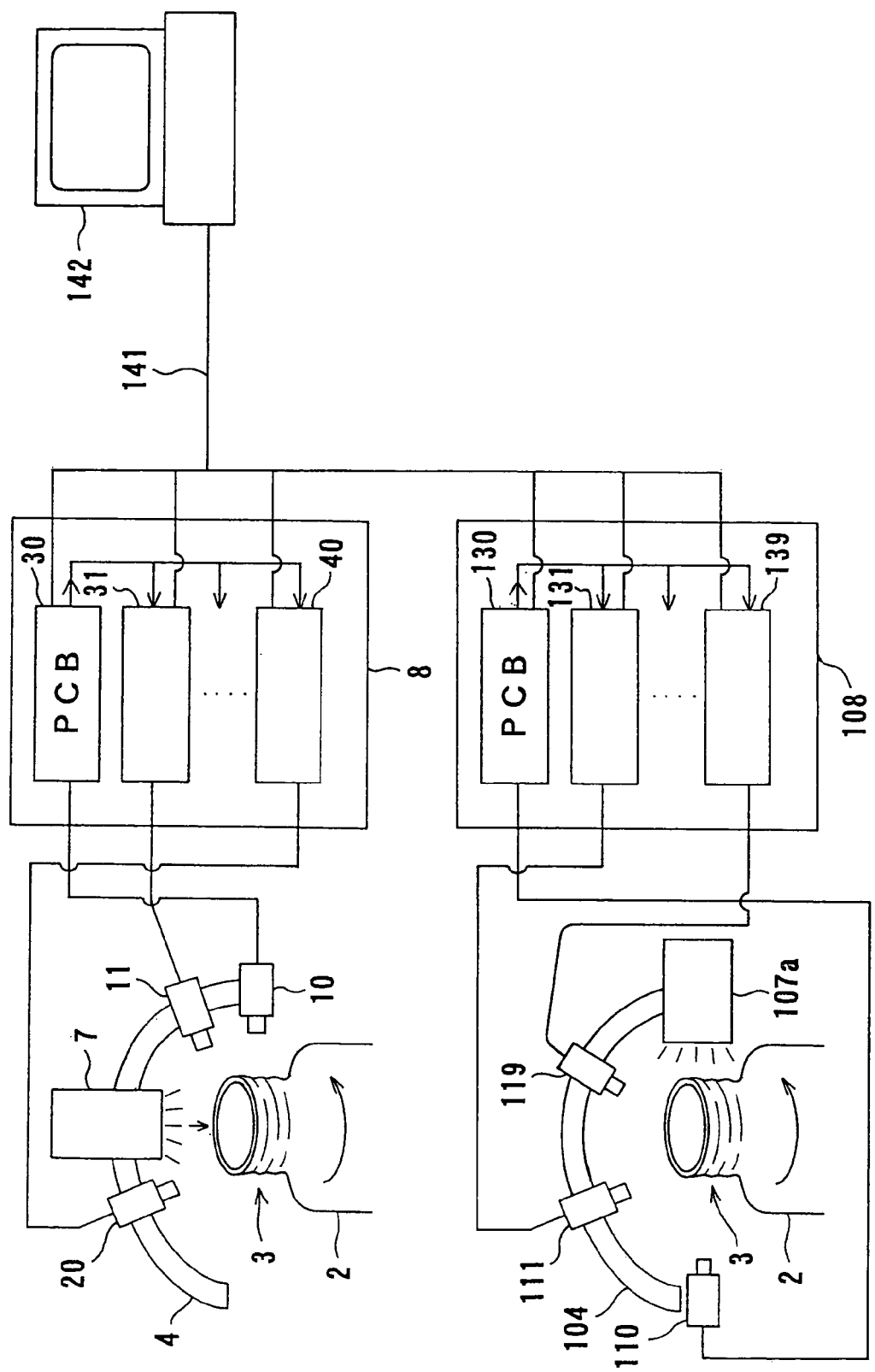

OPTICAL INSPECTION OF GLASS BOTTLES USING MULTIPLE CAMERAS

CROSS-REFERENCE TO PRIOR APPLICATION

This is a U.S. national phase application under 35 U.S.C. §371 of International Parent Application No. PCT/JP2002/010838 filed Oct. 18, 2002. The International Application was published in Japanese on Apr. 29, 2004 as International Publication No. WO 2004/036197 under PCT Article 21(2) the contents of which are incorporated herein in thier enirety.

TECHNICAL FIELD

The present invention relates to a glass bottle inspecting apparatus, and more particularly to a glass bottle inspecting apparatus which can detect a defect at a specific location of a bottle-mouth portion and the like of a glass bottle.

BACKGROUND ART

In producing a glass bottle, a crack such as crazing may be sometimes formed in a wall thickness of a bottle-mouth portion. This crack is referred to as a check. The location of the bottle-mouth portion where a check is generated is limited to some extent, and typically there are a mouth-check generated in the top surface or near the top surface of the bottle mouth, a screw-check generated in a screw thread portion of the bottle mouth, and a neck-check generated in a neck portion of the bottle mouth. Further, depending on the direction of the crack, the checks are classified into a vertical check extending in a vertical direction (substantially vertical direction), a lateral check extending in a lateral direction (substantially horizontal direction), and a skew check extending in an oblique direction.

Because the above-mentioned check can cause damage to the glass bottle, the presence or absence of a check is detected by imaging the bottle-mouth portion, and the glass bottle having the check is removed as a defective bottle.

Conventionally, there has been known an inspecting apparatus for inspecting a check of a glass bottle which can inspect the presence or absence of a check automatically by imaging a bottle-mouth portion of a glass bottle. The check inspecting apparatus comprises plural pairs of light-emitting units and light-receiving units which are arranged so as to surround the bottle-mouth portion of the glass bottle, and the plural pairs of the light-emitting units and the light-receiving units are adjusted and arranged in an optimum position with respect to the bottle-mouth portion of the glass bottle to be inspected. Then, reflected light from the glass bottle is received by each pair of the light-emitting unit and the light-receiving unit, and the obtained signals are processed to detect a check in the bottle-mouth portion. In this case, light emitted from the light-emitting unit is applied to the bottle-mouth portion, and if there is a check, the light is reflected by a crack plane of the check and is thus illuminated brightly. Therefore, the reflected light is received by the light-receiving unit which is the companion to the light-emitting unit, and the check of the bottle portion is detected by judging the presence or absence of a portion having brightness at or exceeding a predetermined value.

The above-mentioned conventional check inspection apparatus has plural inspection stations for inspecting a check in the bottle-mouth portion of the glass bottle, and the glass bottle is held and conveyed along a circumference by a star wheel for inspection, and is then indexed in the plural inspection stations. In the plural inspection stations, while the glass bottle is rotated about its own axis, the glass bottle is inspected to detect each defect such as a mouth-check, a screw-check, or a neck-check individually.

The above-mentioned conventional check inspection apparatus is constructed so that plural inspection stations are provided, and plural pairs of light-emitting units and light-receiving units are arranged in each of the inspection stations. Therefore, when the type of glass bottle to be inspected is changed, the arrangement of the plural pairs of the light-emitting units and the light-receiving units must be readjusted in each of the inspection stations. Specifically, angles and heights of the plural pairs of the light-emitting units and the light-receiving units in each of the inspection stations must be readjusted, and the sensitivity and the like of the light-receiving unit must be readjusted.

Further, in the glass bottle having a screw thread portion on a bottle-mouth portion, the screw thread portion has complicated curved surfaces. Therefore, in many cases, reflected light similar to the reflected light caused by the check is produced in the screw thread portion. However, even if the reflected light is produced from an area where the screw thread portion is located, processing is carried out so as not to judge that there is a check. Therefore, even if there is a check in the screw thread portion and areas above and below the screw thread portion, such a check cannot be detected. Further, the seam portion of the bottle is formed into a curved surface extending continuously in the vertical direction. Therefore, in many cases, reflected light similar to the reflected light caused by the check is produced in this seam portion. Thus, the same processing as in the screw thread portion is carried out in this seam portion. Consequently, even if there is a check in the seam portion and an area around the seam portion, such a check cannot be detected. That is, in a specific part of a glass bottle, even if the glass bottle is normal, an image of the normal glass bottle which has been imaged by a CCD camera becomes the same image as a defective glass bottle. Thus, a non-defective bottle and a defective bottle cannot be distinguished from each other. Further, conventionally, it is difficult to detect a molding failure in the screw thread portion or the like which is generated in molding a bottle.

DISCLOSURE OF INVENTION

In view of the foregoing, it is therefore an object of the present invention to provide a glass bottle inspecting apparatus which can detect a defect at a specific location of a glass bottle such as a defect in areas located above and below a screw thread portion or a defect located around a seam portion of the bottle, and a molding failure in the bottle (particularly, the screw thread portion) without a need for readjustment of the arrangement of light-emitting units and light-receiving units when the type of glass bottle to be inspected is changed.

In order to achieve the above object, according to an aspect of the present invention, there is provided an inspecting apparatus for detecting a defect of a glass bottle by imaging light from the glass bottle while the glass bottle is illuminated and rotated, and processing the obtained image, the inspecting apparatus comprising: a lighting device disposed at a predetermined position with respect to the glass bottle, a plurality of CCD cameras disposed around the glass bottle for imaging a specific part of the glass bottle, an angle detection device for detecting a rotation angle of the glass bottle with respect to a reference position, and an image processor for processing the images obtained by the CCD cameras, wherein the image processor stores rotation angle information detected by the angle detection device in such a manner that the rotation angle information corresponds to the image imaged by each of the CCD cameras.

According to the present invention, light from the lighting device disposed at a predetermined position with respect to the glass bottle is applied to the glass bottle which is rotating, and transmitted light which has passed through a specific part (for example, the bottle-mouth portion) of the glass bottle or reflected light which has reflected from a specific part (for example, the bottle-mouth portion) of the glass bottle is imaged by a plurality of CCD cameras.

On the other hand, a rotation angle of the rotating glass bottle with respect to a reference position is detected by the angle detection device. Then, rotation angle information detected by the angle detection device is stored at a predetermined position, for example, in the image in such a manner that the rotation angle information corresponds to the image imaged by each of the CCD cameras. Therefore, according to the present invention, it is possible to recognize what the degree of imaging angle of the image imaged by each of the CCD cameras with respect to the reference position is.

In a preferred aspect of the present invention, the rotation angle information is written on the image imaged by each of the CCD cameras.

In a preferred aspect of the present invention, the image processor detects the defect at a specific part of the glass bottle by comparing the image having the rotation angle information with a reference image prepared in advance and having the same corresponding rotation angle information.

According to the present invention, the reference image is prepared in each angle in advance, and an actual image having angle information obtained by imaging the glass bottle to be inspected is compared with the reference image, and hence a defect at a specific part of the glass bottle can be detected. Therefore, if the reference image is prepared in each angle on the basis of the glass bottle having no defect (non-defective bottle), a defect at a specific part of the glass bottle can be detected by judging whether the actually obtained image in each angle has an area different from the reference image.

In a preferred aspect of the present invention, the reference image is produced in advance on the basis of the images of glass bottles having no defect.

In a preferred aspect of the present invention, mold information is stored in such a manner that the mold information corresponds to the image imaged by each of the CCD cameras.

In a preferred aspect of the present invention, information related to production including manufacturing number, manufacturing line, or manufacturing date and time is stored in such a manner that the information corresponds to the image imaged by each of the CCD cameras.

In a preferred aspect of the present invention, an inspection result is stored in such a manner that the inspection result corresponds to the image imaged by each of the CCD cameras.

BRIEF DESCRIPTION OF DRAWINGS

FIG. 2 is a plan view of a hemispherical member of the inspecting apparatus shown in FIG. 1;

FIG. 5 is a schematic view showing an example of an image on which angle information and the mold number are written;

FIG. 6 is a schematic view showing an image of a glass bottle as a sample;

FIG. 11A is a schematic view showing a bright template and FIG. 11B is a schematic view showing a dark template;

FIG. 14 is a view taken along line A-A of FIG. 13;

FIG. 17 is a schematic view showing the relationship between an image processor and CCD cameras in the inspecting apparatus according to the second embodiment of the present invention.

BEST MODE FOR CARRYING OUT THE INVENTION

A glass bottle inspecting apparatus according to an embodiment of the present invention will be described with reference to FIGS. 1 through 7. In the embodiment of the glass bottle inspecting apparatus of the present invention, a case where a specific part of a glass bottle to be inspected corresponds to a bottle-mouth portion and a defect to be inspected is a check in the bottle-mouth portion or a molding failure in a screw thread portion or the like will be described.

A glass bottle to be inspected is held by a star wheel for inspection (not shown), and is conveyed along a conveyance path on a circumference of the star wheel. The glass bottle inspecting apparatus according to the present invention is disposed in one station (first inspection station) at a certain place in the conveyance path on the circumference of the star wheel. In the first inspection station, the glass bottle conveyed by the star wheel is indexed, and a check in a bottle-mouth portion or a molding failure in a screw thread portion or the like is detected by the glass bottle inspecting apparatus according to the present invention.

Figure 1:
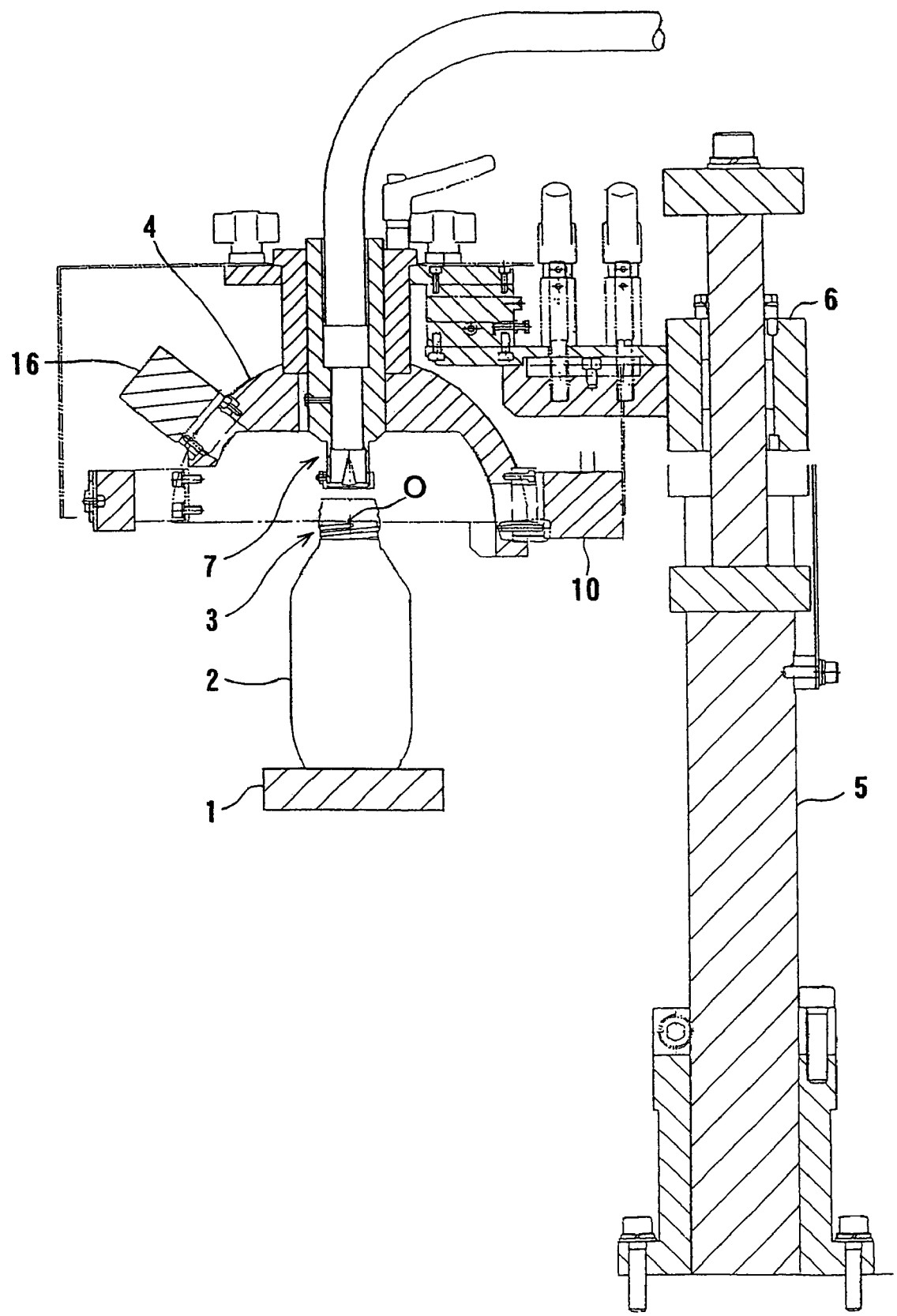
FIG. 1 is a vertical cross-sectional view of an inspecting apparatus according to a first embodiment of the present invention.

FIG. 1 is a vertical cross-sectional view showing a glass bottle inspecting apparatus according to a first embodiment of the present invention. As shown in FIG. 1, the inspecting apparatus comprises a hemispherical member 4 disposed so as to cover a bottle-mouth portion 3 of a glass bottle 2 placed on a rotatable turntable 1, and a support 5 for supporting the hemispherical member 4. The center O of the hemispherical member 4 is substantially aligned with the bottle-mouth portion 3 of the glass bottle 2 placed on the turntable 1. The hemispherical member 4 is attached to the support 5 through a sliding member 6 which is vertically movable, and is configured to be movable vertically with respect to the support 5.

FIG. 2 is a plan view of the hemispherical member 4 shown in FIG. 1. As shown in FIGS. 1 and 2, a lighting device 7 for applying light to the interior of the bottle mouth of the glass bottle 2 on the turntable 1 is disposed on the top portion of the hemispherical member 4, i.e., above the top surface of the bottle-mouth portion 3 of the glass bottle 2 on the turntable 1. Further, a plurality of CCD cameras 10-20 are disposed on the hemispherical member 4 so as to surround the bottle-mouth portion 3 of the glass bottle 2. The optical axes of the CCD cameras 10-20 are located on lines extending radially from the center O of the hemispherical member 4 (the bottle-mouth portion 3 of the glass bottle 2).

In the present embodiment, a total of 11 CCD cameras are provided and one of the cameras 10 constitutes an angle detection camera for detecting a rotation angle of the glass bottle 2 with respect to a predetermined reference position by imaging a screw thread on the bottle-mouth portion 3 of the glass bottle 2 placed on the turntable 1. As shown in FIG. 1, the angle detection camera 10 is arranged so that an angle of elevation of its optical angle is equal to 0 degrees, and can image the screw thread on the bottle-mouth portion 3 of the glass bottle 2 from a horizontal direction.

The cameras 11-20 other than the angle detection camera 10 constitute the inspecting CCD cameras for inspecting a check of the bottle-mouth portion 3 by imaging the bottle-mouth portion 3 from various angular directions. In the present embodiment, the inspecting CCD cameras 11-20 are arranged so that angles between the optical axes of the respective cameras projected on the horizontal plane and the optical axis of the angle detection camera 10 are 25 degrees (as for a first inspecting CCD camera 11 and a second inspecting CCD camera 12), 59.5 degrees (as for a third inspecting CCD camera 13), 140 degrees (as for a fourth inspecting CCD camera 14 and a fifth inspecting camera 15), 185 degrees (as for a sixth inspecting CCD camera 16), 220 degrees (as for a seventh inspecting CCD camera 17), 260 degrees (as for an eighth inspecting CCD camera 18), 296.5 degrees (as for a ninth inspecting CCD camera 19), and 326 degrees (as for a tenth inspecting CCD camera 20), respectively.

Further, an angle of elevation of the optical axis of the first inspecting CCD camera 11 is 30 degrees, an angle of elevation of the optical axis of the second inspecting CCD camera 12 is 0 degrees, an angle of elevation of the optical axis of the fourth inspecting CCD camera 14 is 55 degrees, an angle of elevation of the optical axis of the fifth inspecting CCD camera 15 is 15 degrees, an angle of elevation of the optical axis of the sixth inspecting CCD camera 16 is 45 degrees, an angle of elevation of the optical axis of the seventh inspecting CCD camera 17 is 20 degrees, an angle of elevation of the optical axis of the eighth inspecting CCD camera 18 is 35 degrees, and an angle of elevation of the optical axis of the tenth inspecting CCD camera 20 is 25 degrees. The third inspecting CCD camera 13 and the ninth inspecting CCD camera 19 are configured to be movable up and down on the surface of the hemispherical member 4, and hence the angles of elevation of the optical axes of the third inspecting CCD camera 13 and the ninth inspecting CCD camera 19 can be freely set.

The number of pixels of each of the CCD cameras 10-20 used in the present embodiment is 64×64, and one image can be imaged at intervals of 0.4 milliseconds. For example, in the case of inspecting 300 glass bottles in one minute, the processing time of one glass bottle is 200 milliseconds. In the case where the glass bottle is imaged for 100 milliseconds during the processing time, 250 images (=100/0.4) for each glass bottle can be imaged at a maximum. While the bottle-mouth portion 3 of the glass bottle 2 is inspected by the inspecting apparatus, the turntable 1 rotates, and the glass bottle 2 is imaged simultaneously by the CCD cameras 10-20 as the glass bottle 2 is rotated. In this manner, while the glass bottle 2 is rotated, the glass bottle 2 is repeatedly imaged, and hence the bottle-mouth portion 3 of the glass bottle 2 can be imaged over the full circumference of the bottle-mouth portion 3.

Figure 3:
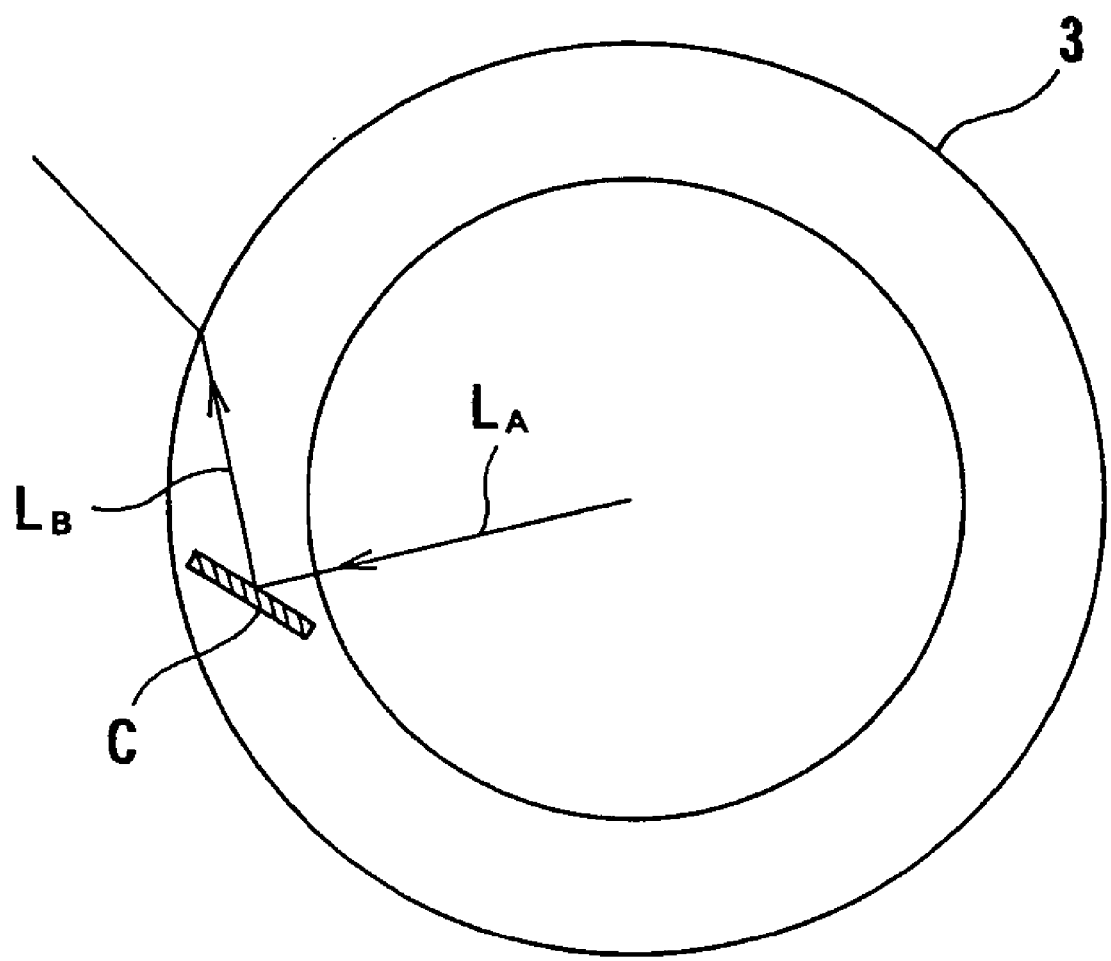
FIG. 3 is a schematic view showing the behavior of light from a lighting device according to the first embodiment of the present invention.

Here, light from the lighting device 7 disposed above the glass bottle 2 is applied to the interior of the bottle mouth of the glass bottle 2, and as shown in FIG. 3, part of the light $L_A$ is incident into the bottle-mouth portion 3 from the inner circumferential surface of the bottle-mouth portion 3. If there is a check C inside the bottle-mouth portion 3, the light $L_A$ is reflected by the crack plane of the check C inside the bottle-mouth portion 3, and the reflected light $L_B$ passes through the bottle-mouth portion 3 and is imaged by the inspecting CCD cameras 11-20. The light $L_B$ reflected by the crack plane of the check C is brighter than light which has passed through other parts, and hence the part corresponding to the check C becomes a brighter area than other parts in the image which has been imaged by the CCD camera. The image processor provided in the inspecting apparatus detects such a brighter area in the image obtained by each of the above CCD cameras 10-20 and judges the brighter area to be a check. On the other hand, if there is no check C inside the bottle-mouth portion 3, part of the light $L_A$ is incident into the bottle-mouth portion 3 from the inner circumferential surface of the bottle-mouth portion 3 and passes through the bottle-mouth portion 3. In this case, if there is a molding failure in the screw thread portion or the like, the light from the molding failure part is scattered in directions where such light is not incident on the corresponding CCD cameras. Thus, the image becomes dimmer and blurrier than the image of the normally molded screw thread portion, and hence the molding failure can be detected.

Figure 4:
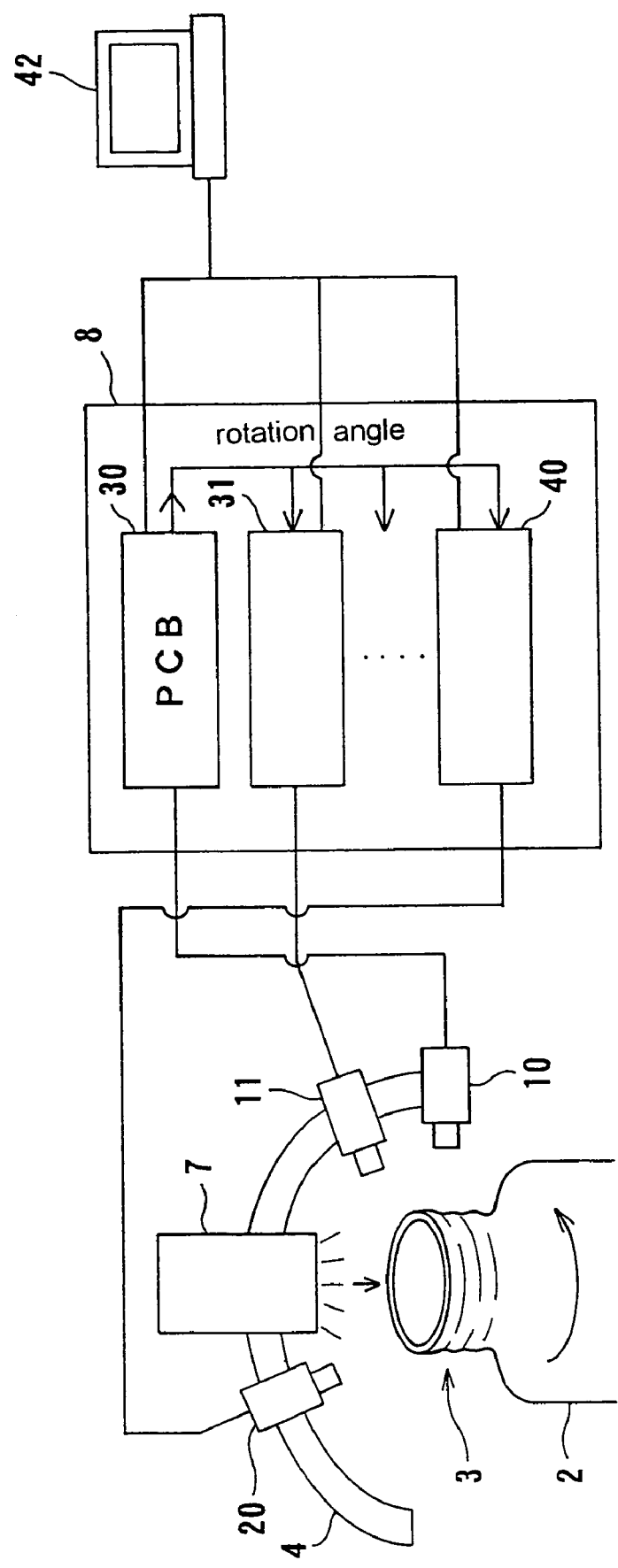
FIG. 4 is a schematic view showing the relationship between an image processor and CCD cameras in the inspecting apparatus according to the first embodiment of the present invention.

FIG. 4 is a schematic view showing the relationship between the image processor and the respective CCD cameras 10-20. As shown in FIG. 4, the image processor 8 has computing boards 30-40 corresponding to the CCD cameras 10-20, and these computing boards 30-40 are connected to the corresponding CCD cameras 10-20, respectively.

The relationship between the height position of the spiral of the screw thread on the glass bottle 2 and the rotation angle of the glass bottle 2 with respect to a predetermined reference position is stored in advance in the angle detection computing board 30 connected to the angle detection camera 10. The angle detection computing board 30 detects the height position of the spiral of the screw thread from the image obtained by the angle detection camera 10, and then detects the rotation angle of the glass bottle 2 at the time of imaging with respect to the reference position from the height position of the spiral of the screw thread on the basis of the above relationship. Signals of the detected rotation angles of the glass bottle 2 are sent to the computing boards 31-40 connected to the respective inspecting CCD cameras 11-20. Thus, the angle detection camera 10 and the angle detection computing board 30 constitute an angle detection device for detecting the rotation angle of the glass bottle with respect to the reference position at the time of imaging.

As described above, the rotation angle of the glass bottle 2 which has been sent from the angle detection computing board 30 is sent to the computing boards 31-40 connected to the respective inspecting CCD cameras 11-20, and the rotation angle is written as rotation angle information on each of the images which have been imaged by the respective inspecting CCD cameras 11-20.

Next, the operation of the glass bottle inspecting apparatus having the above structure will be described with reference to FIGS. 1 through 4.

As described above, diffused light from the lighting device 7 is applied to the interior of the bottle mouth from an upper part of the bottle-mouth portion 3 of the glass bottle 2 placed on the turntable 1. The diffused light which has been applied to the interior of the bottle mouth is radially diffused and passes through the bottle-mouth portion 3. Then, the transmitted light which has radially passed through the bottle-mouth portion 3 is simultaneously imaged by all of the CCD cameras (11 CCD cameras) 10-20 disposed around the bottle-mouth portion 3. At this time, as described above, one CCD camera constitutes an angle detection camera, and this angle detection camera 10 images the thread screw on the bottle-mouth portion 3 to detect a rotation angle of the glass bottle with respect to the reference position at the time of imaging. When the spiral of the screw thread makes one revolution, the height position is changed by one pitch. Therefore, if the relationship between the height position of the spiral of the screw thread and the rotation angle with respect to the reference position is stored beforehand in the computing board 30 of the angle detection camera 10, then the angle detection camera 10 can detect an angle with respect to the reference position at the time of imaging. As the reference position, for example, the starting end which is the start of the screw thread is taken as the reference position (0 degrees).

In a case where the angle detection camera 10 is taken as a reference, the relative positions of the respective inspecting CCD cameras 11-20 to the angle detection camera 10 are predetermined. Therefore, by displacing the reference position relatively, the rotation angle detected by the computing board 30 of the angle detection camera 10 can be used as a rotation angle when the respective inspecting CCD cameras 11-20 image the bottle-mouth portion 3. Therefore, in the present embodiment, the rotation angle which has been transmitted from the angle detection computing board 30 of the angle detection camera 10 is written on each of the images which have been imaged by the respective inspecting CCD cameras 11-20.

While the glass bottle 2 is rotated by the turntable 1, the transmitted light which has passed through the bottle-mouth portion 3 is imaged at intervals of predetermined time to obtain a large number of images. Then, the angle information at the time of imaging is written on all of the images.

On the other hand, a glass bottle molding machine has a large number of molds, and a large number of bottles are simultaneously formed by these molds. It is known that the property (wall thickness, delicate shape, and the like) of the molded glass bottle largely depends on the mold. Further, the generation of a check in the bottle-mouth portion of the glass bottle depends on the mold. Therefore, information of the mold number for recognizing which mold forms such a glass bottle is written on the image of the glass bottle obtained by the inspecting apparatus of the present invention. The mold number can be detected by a mold number reading apparatus which reads convex marks formed on the bottle bottom of the glass bottle. Signals from the mold number reading apparatus are inputted into the computing boards 31-40 of the respective inspecting CCD cameras 11-20, and the mold number is written on each of the images. Further, information related to production such as manufacturing number is written on each of the images. FIG. 5 is a schematic view showing an example of an image on which rotation angle information and the mold number obtained in the above manner are written. Inspection results, for example, a result about whether the glass bottle is non-defective or defective may be written on each of the images.

Next, each image on which angle information, the mold number, and the like are written is compared with a reference image called a template which is prepared before inspection of the glass bottle, and the presence or absence of a check in the bottle-mouth portion of the glass bottle is determined. In this process, since the reference image (template) is prepared for each angle and each mold number, the reference image corresponding to the angle information and the mold number which have been written on the image obtained by each of the inspecting CCD cameras is selected, and an image of the glass bottle to be inspected is compared with the selected reference image.

Next, a method of producing a reference image (template) will be described.

A method of producing a reference image (hereinafter referred to as template when it is considered proper) comprises three processes which are roughly classified. Specifically, the method comprises an imaging process for imaging a plurality of glass bottles used for producing a template by the CCD cameras, an image selection process for selecting images of non-defective glass bottles from a group of the images imaged by the imaging process by removing images of defective glass bottles, and an image producing process for producing a template on the basis of the images selected by the image selecting process. Next, the respective processes will be described in order.

(1) Imaging Process

Basic data of the imaging process carried out in the present embodiment are as follows:

① The number of glass bottles used as samples 100
② Molding numbers M1-M8
③ Angles A1-A8 (A1: 0-45°, A2: 45-90°, . . . , A8: 315-360°)
④ The number of images per one glass bottle 100

One hundred glass bottles serving as samples are transferred to an inspection station by an inspecting star wheel, and are imaged by the first through tenth inspecting CCD cameras 11-20 provided in the inspection station. The obtained images are sent to a computer 42 (see FIG. 4) connected to the computing boards 30-40 of the respective inspecting CCD cameras 11-20, and the following processes are carried out by the computer 42 on the basis of these images.

Next, an example of producing a template corresponding to the first inspecting CCD camera 11, the molding number M1, and the angle A1 will be described below.

As described above, 100 images per one glass bottle are imaged, and a total of 10,000 images per 100 glass bottles are imaged by the first inspecting CCD camera 11. In the case where there are three glass bottles molded by the mold number M1 among 100 glass bottles, the number of images of the glass bottles formed by the mold number M1 is 3×100=300. Therefore, first, 300 images of the glass bottles molded by the mold number M1 are selected from 10,000 images. Further, the images which have been imaged in the angle A1 are selected from the 300 images. In the present embodiment, 35 images are imaged in the angle A1. Therefore, 35 images are selected to produce a template corresponding to the mold number M1 and the angle A1.

(2) Image Selecting Process

If a defective glass bottle is included in a plurality of glass bottles used as samples in producing a template serving as a reference image, then a template containing light caused by a check is produced. Thus, if the template is produced on the basis of the image containing bright light from the location where bright light should not be created, then the glass bottle having a check at such a location cannot be judged to be a defective glass bottle. For this reason, as a preprocess for producing a template, work for removing images of defective glass bottles from a plurality of images used for the template is carried out.

Figure 7:
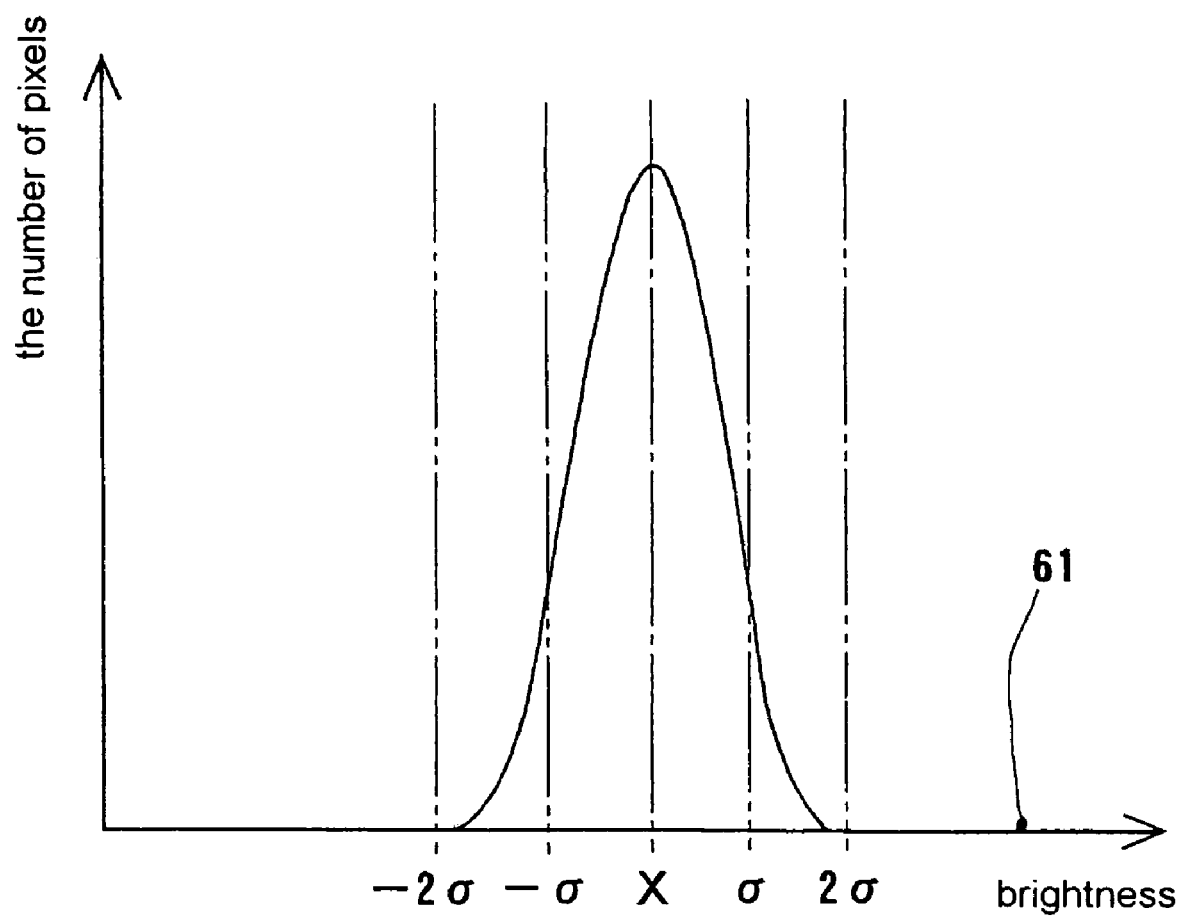
FIG. 7 is a histogram showing brightness distribution of pixels.

In the image selecting process, a frequency distribution showing the brightness distribution of each pixel forming an image is produced on the basis of a plurality of images selected by the imaging process. FIG. 6 is a schematic view showing an image of a glass bottle as a sample. FIG. 7 is a histogram showing the brightness distribution of pixels. In FIG. 6, reference numeral 50 represents bright areas. In FIG. 7, the vertical axis of frequency distribution represents the number of pixels, and the horizontal axis represents brightness (0-255).

As shown in FIG. 6, the image of each of the CCD cameras 11-20 is composed of a group of pixels comprising 64 vertical pixels×64 horizontal pixels. The number of pixels can be suitably adjusted. In this example, one image is decomposed into 64×64 pixels. Then, the pixels in the first row, the first column from the decomposed pixel group are plotted on the graph for each image. In this manner, the pixels in the first row, the first column for each of 35 images are plotted on the graph successively, and a frequency distribution showing the brightness distribution of the pixels in the first row, the first column can be obtained. The frequency distribution is produced beginning with the first row, the first column and continuing to the 64th row, the 64th column.

Next, the standard deviation σ representing dispersion of brightness is calculated for every obtained frequency distribution. The standard deviation σ is obtained by a general statistical method. Then, detection criterion are set so that the image is judged to be an image of a non-defective glass bottle when the brightness of pixels is distributed within a range of ±2σ, for example. In the case where all of the glass bottles serving as samples are non-defective glass bottles, the brightness of all pixels is distributed in the vicinity of a substantially average value X. Therefore, as shown in FIG. 7, all of the pixels exist within a range of ±2σ. In this case, no image is removed, and all 35 images are used for producing a template.

On the other hand, when a glass bottle has a check, the part 60 on the image representing the presence of a check becomes extremely bright (see FIG. 6). Then, in the frequency distribution, as shown in FIG. 7, the number of pixels, which is represented by a reference numeral 61, having brightness corresponding to the part 60 is plotted in the area to the right of +2σ. Then, it is judged that a check is imaged on the image having such pixels. Further, similarly, in the case where there is an extremely dark part, the number of pixels having brightness corresponding to the dark part is plotted in the area to the left of −2σ. Then, the screw thread portion or the like having a molding failure is judged to be imaged on the image having such pixels. Then, these images are removed from the images used for producing a template. In the present embodiment, the image selecting process is carried out using the statistical method. However, the method is not limited to the statistical method, and any method can be used as long as the image to be removed can be specified. For example, a plurality of images which have been obtained by the imaging process may be displayed on a display both for mold numbers and for angles, and an image of a defective glass bottle may be selected by observing the image on the display by an operator.

(3) Image Producing Process

Figure 8:
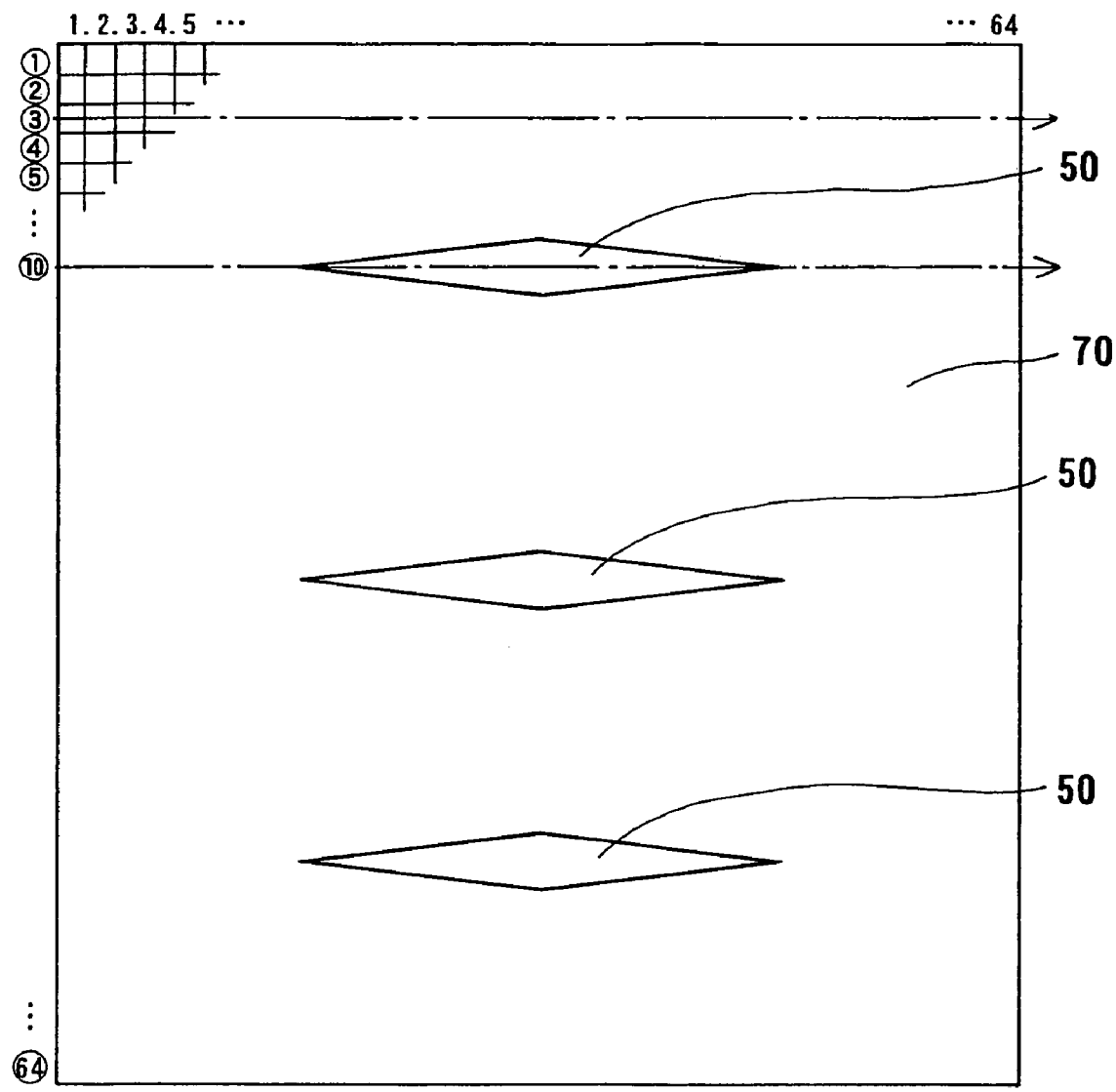
FIG. 8 is a schematic view showing an image of a non-defective glass bottle.
Figure 9:
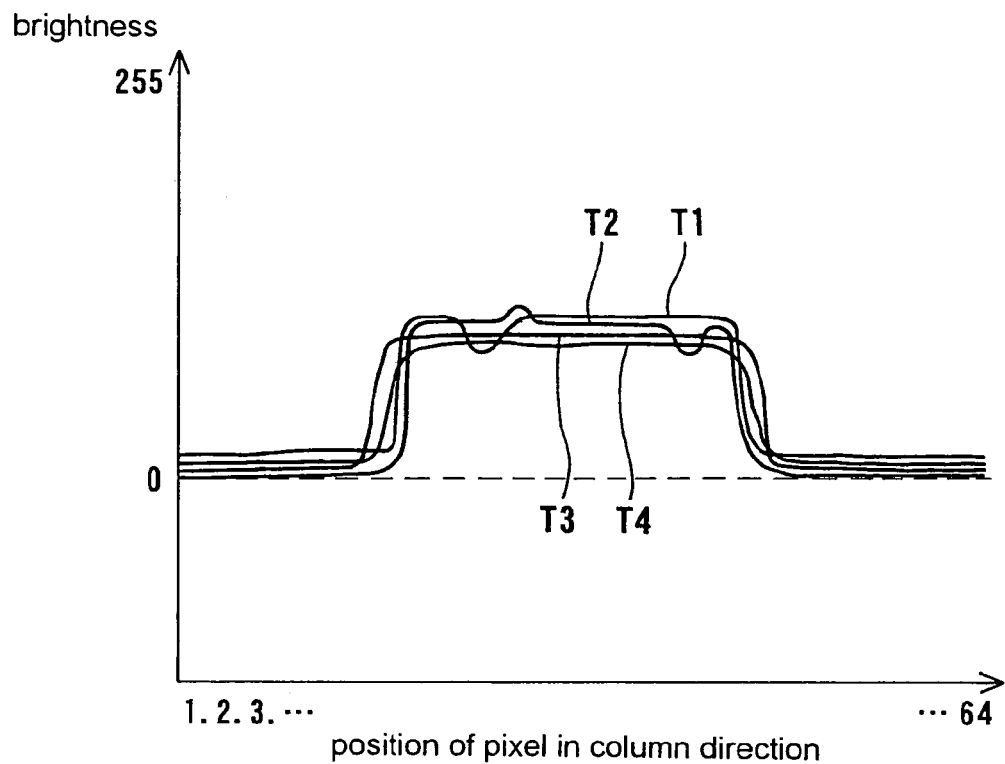
FIG. 9 is a graph showing brightness distribution of pixels in a certain row.
Figure 10:
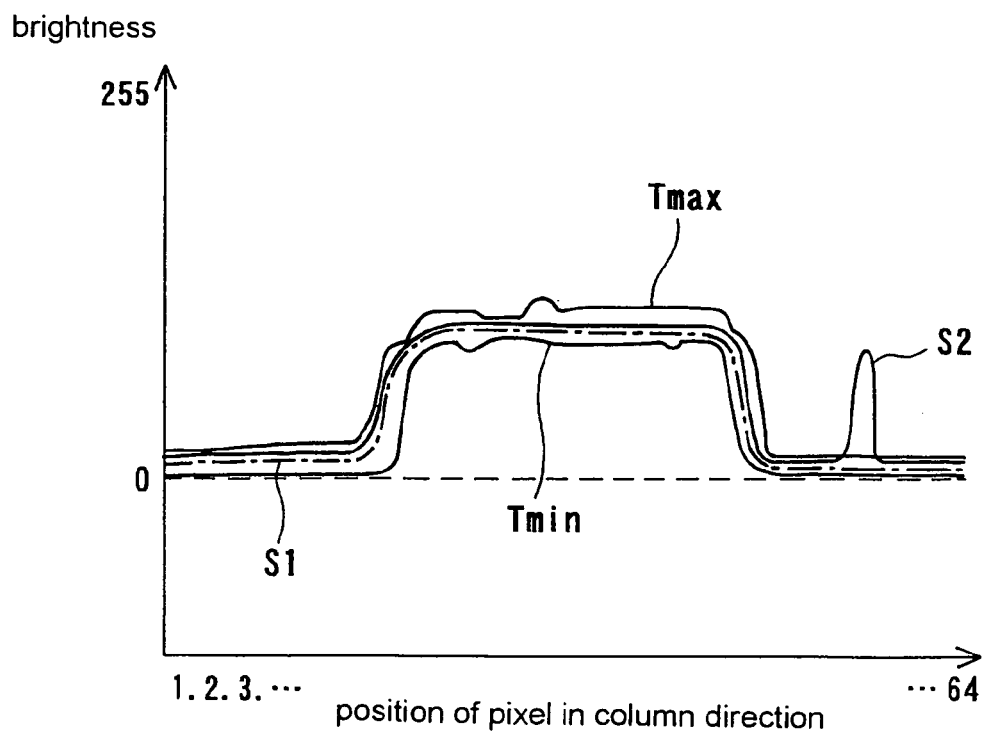
FIG. 10 is a view showing the relationship between a template and brightness distribution of each pixel in an image of a glass bottle to be inspected.

In the image producing process, reference images for a template are produced on the basis of a plurality of images selected in the above image selecting process. The image producing process will be described with reference to FIGS. 8 through 10. FIG. 8 is a schematic view showing an image of a non-defective glass bottle. FIG. 9 is a graph showing the brightness distribution of pixels in a certain row. FIG. 10 is a view showing the relationship between a template and brightness distribution of each pixel in an image of a glass bottle to be inspected.

In the present embodiment, the template is produced for each pixel row of the image. First, a certain pixel row is specified. For example, in FIG. 8, the third row is specified. Next, the specified pixel row is scanned in the column direction (lateral direction of FIG. 8, the direction of 1, 2, 3 . . . 64), and the brightness of each pixel is represented on the graph. Specifically, each pixel on the specified pixel row is plotted on the graph where the vertical axis represents brightness of pixels and the horizontal axis represents column numbers of pixels. As shown in FIG. 8, since the pixels in the third row are located in the dark part 70, a line drawn by plotting the respective pixels in the third row on the graph becomes a straight line located in the vicinity of brightness 0.

On the other hand, for example, in the case where the pixels in the tenth row are specified, a line drawn by plotting the respective pixels in the tenth row becomes T1 shown in FIG. 9. Specifically, in the tenth row, since the bright part 50 formed by light from the screw thread portion is scanned, the pixels corresponding to the bright part 50 show a high brightness.

Further, with regard to all the images, all the pixels in the same row are plotted on one graph. Specifically, in the present embodiment, since 35 images are used for producing a template, as shown in FIG. 9, a brightness distribution chart composed of a group of 35 lines (in FIG. 9, only four lines T1-T4 are shown) is produced. In this manner, brightness distribution charts are produced for all of the rows from the first row to the 64th row.

Then, the maximum area demarcated by a group of these lines becomes an area which should be taken as a template. Specifically, as shown in FIG. 10, the line obtained by connecting points representing the maximum value (maximum brightness) in each column is taken as a bright template line Tmax, and the line obtained by connecting points representing the minimum value (minimum brightness) in each column is taken as a dark template line Tmin. An area enclosed by the bright template line Tmax and the dark template line Tmin becomes a reference image (template) to be determined. That is, a range between the maximum brightness and the minimum brightness is continuously formed in the column direction between the bright template line Tmax and the dark template line Tmin. In this manner, 64 templates are produced corresponding to the mold number M1 and the angle A1.

Because work for producing these templates is conducted on the mold numbers M1-M20 and the angles A1-A8, 64×20×8=10,240 templates are given to the first inspecting CCD camera 11. Specifically, each of the inspecting CCD cameras 11-20 has templates for each mold, each angle, and each pixel. As described above, since the property of the glass bottle and the generation of a check largely depend on a mold, the accuracy in detection of a check or a molding failure in the screw thread portion or the like can be enhanced by producing templates corresponding to each of the molds.

Next, there will be described a method of judging the presence or absence of a check in a bottle-mouth portion or a molding failure in a screw thread portion or the like by comparing the reference image (template) obtained by the above method and the image obtained from the glass bottle to be inspected.

First, the templates produced under the same condition (mold, angle, and the like) as the images to be inspected are selected for comparing an object on the basis of various information such as angle information, the mold number, and the like given to the image. Next, the image of the glass bottle to be inspected is compared with the templates in each pixel row. Specifically, the line representing brightness distribution in the column direction in a specific pixel row is compared with a template. Then, as shown in FIG. 10, if the line S1 representing brightness of the glass bottle to be inspected is located completely in a non-defective article area of the template (area enclosed by the bright template line Tmax and the dark template line Tmin), then this glass bottle is judged to be a non-defective article.

On the other hand, as shown by line S2, if part of the line is outside the non-defective article area of the template, this glass bottle is judged to be a defective article. Then, when all of the pixel rows are compared with the templates, and at least one row is judged to be defective, it is judged that this glass bottle has a check in the bottle-mouth portion or a molding failure in the screw thread portion or the like.

Such inspection is carried out in each of the angles A1-A8. Therefore, even if it is judged that there is neither a check nor a molding failure in the angle A1, for example, in some cases, it is judged that there is a check or a molding failure in the angle A2. In the present embodiment, because the detection of a check or a molding failure is carried out in a plurality of angles (A1-A8), the accuracy in inspection of a check or a molding failure can be enhanced, compared with the conventional inspection apparatus.

The 64 templates produced in the above manner may be integrated into a two-dimensional (planar) bright template and a two-dimensional (planar) dark template. FIG. 11A is a schematic view showing a bright template and FIG. 11B is a schematic view showing a dark template. Next, a process of producing the bright template will be described with reference to FIGS. 10 and 11A.

As shown in FIG. 10, the brightness of the bright template line Tmax in a certain row can be digitized in the range of 0 to 255 in each column. The respective numerical value representing the brightness is plotted in a corresponding row in a table composed of 64 rows×64 columns shown in FIG. 11A. For example, the numerical value representing the brightness held by the m column of the bright template line Tmax in the n row is plotted in a section located in the n row, the m column of the table. In FIG. 11A, the brightness ranging from 0 to 255 is represented by hexadecimal notation.

Figure 12A:
FIG. 12A is a view showing a bright template image imaged on the basis of numerical values of the bright template shown in FIG. 11A.
Figure 12B:
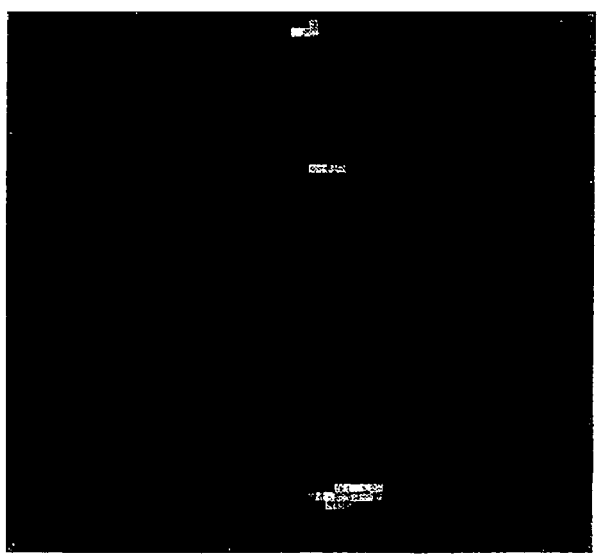
FIG. 12B is a view showing a dark template image imaged on the basis of numerical values of the dark template shown in FIG. 11B.

When all of the brightness of the bright template line Tmax from the first to the 64th row have been plotted in the table, one bright template as shown in FIG. 11A is produced. The dark template shown in FIG. 11B is also produced on the basis of the dark template line Tmin in the same process as the bright template. The range between the maximum brightness and the minimum brightness in each pixel constituting the reference image is determined by the thus obtained bright template and dark template. Specifically, in an example shown in FIGS. 11A and 11B, the range between the minimum brightness and the maximum brightness in the pixel located in the n row, the m column is from 02 to 08. FIG. 12A is a view showing a bright template image imaged on the basis of numerical values of the bright template shown in FIG. 11A, and FIG. 12B is a view showing a dark template image imaged on the basis of numerical values of the dark template shown in FIG. 11B.

In the above description, an example in which the brightness of all pixels in each row is digitized in producing a two-dimensional (planar) bright template and a two-dimensional (planar) dark template is described. However, a two-dimensional bright template and a two-dimensional dark template may be produced by digitizing the brightness of each pixel not in each row but in each pixel.

The next description is made for a method of judging the presence or absence of a check in the bottle-mouth portion and a molding failure in the screw thread portion or the like in the glass bottle to be inspected by using the bright template and the dark template obtained by the above process. First, the specific row of the image of the glass bottle to be inspected is scanned in the column direction (lateral direction), and the brightness of all pixels in the row is digitized. Next, it is judged whether the brightness of each pixel from the first column to the 64th column in the row exists in a range (hereinafter referred to as the non-defective article range) between the maximum brightness and the minimum brightness determined by the bright template and the dark template. This process is conducted on all the rows from the first row to the 64th row.

Then, if the brightness of all the pixels constituting the image to be inspected exists within the non-defective article range, it is judged that there is neither a check in the bottle-mouth portion nor a molding failure in the screw thread portion or the like in the glass bottle. On the other hand, if the number of pixels which deviate from the non-defective article range by an allowable value or more is not less than a predetermined number, the image is judged to be an image of a defective glass bottle, and it is judged that there is a check in the bottle-mouth portion or a molding failure in the screw thread portion or the like in this glass bottle. The allowable value related to the non-defective article range and the predetermined number of pixels serving as a criterion for judgment of the defective article can be set according to the inspection accuracy to be achieved. For example, if a predetermined number of pixels adjacent to each other in a certain image have brightness outside the non-defective article range, then such an image may be judged to be an image of a defective glass bottle.

In the embodiment shown in FIGS. 1 through 12A and 12B, the interior of the bottle mouth of the glass bottle is illuminated, and a check or a molding failure is detected from the transmitted light which has passed through the bottle-mouth portion. With this arrangement, a lateral check extending in a lateral direction and a skew check extending in an oblique direction can be perfectly detected. Further, most of the vertical checks extending in the vertical direction can be also detected. However, if the crack plane of the vertical check is completely aligned with the direction extending radially from the axis of the bottle, the transmitted light which passes through the bottle-mouth portion travels in a direction parallel to the crack plane. Thus, there is a chance that the vertical check cannot be detected. Therefore, according to the second embodiment, a second inspection station is disposed at a certain place in the conveyance path on the circumference of the star wheel, and a glass bottle inspecting apparatus for detecting a vertical check with reflected light is provided in the second inspection station. It is a matter of course that the inspecting apparatus which uses the transmitted light shown in FIGS. 1 through 12A and 12B is provided in the first inspection station.

Next, a glass bottle inspecting apparatus for detecting a vertical check will be described with reference to FIGS. 13 through 16.

Figure 13:
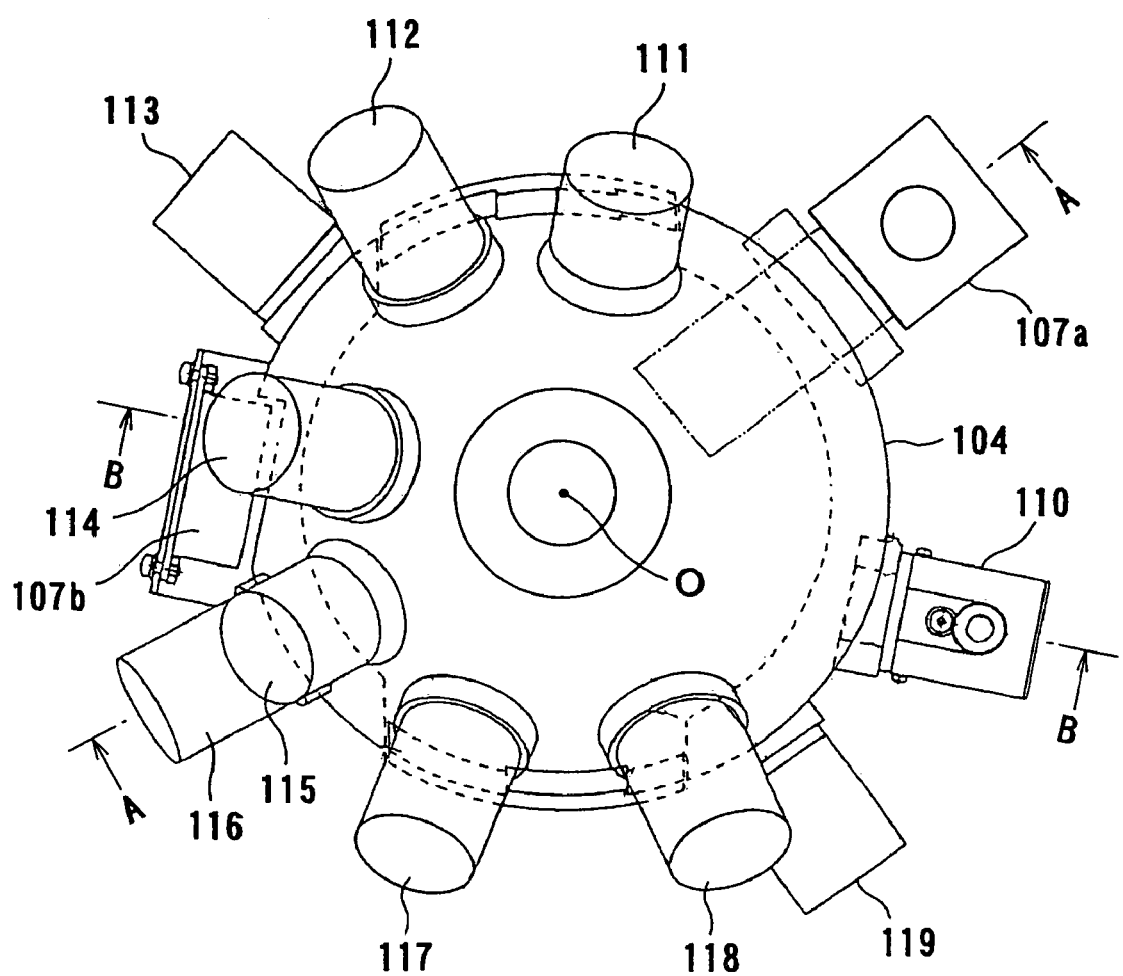
FIG. 13 is a plan view showing the main parts of an inspecting apparatus according to a second embodiment of the present invention.
Figure 15:
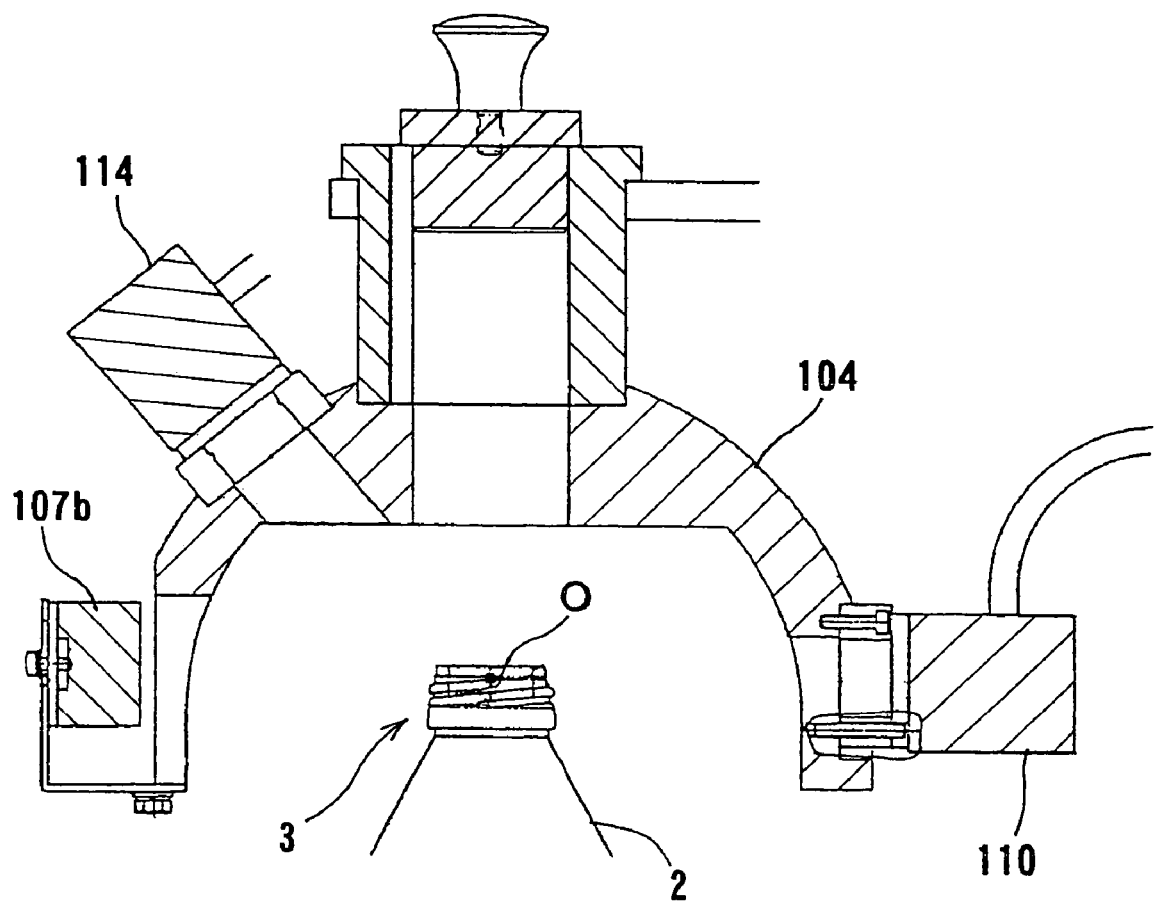
FIG. 15 is a view taken along line B-B of FIG. 13.

FIG. 13 is a plan view showing the main parts of an inspecting apparatus according to a second embodiment of the present invention, FIG. 14 is a view taken along line A-A of FIG. 13, and FIG. 15 is a view taken along line B-B of FIG. 13. As shown in FIGS. 13 through 15, the inspection apparatus has a hemispherical member 104 disposed so as to cover a bottle-mouth portion 3 of a glass bottle 2. The center O of the hemispherical member 104 is substantially aligned with the bottle-mouth portion 3 of the glass bottle 2. A first lighting device 107a for applying light to the bottle-mouth portion 3 of the glass bottle 2 is provided on one side of the hemispherical member 104, i.e., at the side of the bottle-mouth portion 3 of the glass bottle 2. Further, a plurality of CCD cameras 110-119 are disposed on the hemispherical member 104 so as to surround the bottle-mouth portion 3 of the glass bottle 2. The optical axes of the CCD cameras 110-119 are located on lines extending radially from the center O of the hemispherical member 104 (the bottle-mouth portion 3 of the glass bottle 2).

In the present embodiment, a total of 10 CCD cameras are provided and one of the cameras 110 constitutes an angle detection camera for detecting a rotation angle of the glass bottle 2 by imaging a screw thread on the bottle-mouth portion 3 of the glass bottle 2. As shown in FIG. 15, the angle detection camera 110 is arranged so that an angle of elevation of its optical axis is equal to 0 degrees, and can image the screw thread on the bottle-mouth portion 3 of the glass bottle 2 from a horizontal direction. A second lighting device 107b is disposed on the side of the hemispherical member 104 facing the angle detection camera 110, and the screw thread on the bottle-mouth portion 3 of the glass bottle 2 is illuminated by the second lighting device 107b. Light emitted from the second lighting device 107b comprises infrared light, and does not interfere with the light emitted from the first lighting device 107a. The angle detection camera 110 is configured to receive only infrared light emitted from the second lighting device 107b.

The cameras 111-119 other than the angle detection camera 110 constitute inspecting CCD cameras for inspecting a check of the mouth portion 3 by imaging the mouth portion 3 from various angular directions. In the present embodiment, the inspecting CCD cameras 111-119 are arranged so that angles between the optical axes of the respective cameras projected on the horizontal plane and the optical axis of the angle detection camera 110 are 90 degrees (as for a first inspecting CCD camera 111), 130 degrees (as for a second inspecting CCD camera 112), 150 degrees (as for a third inspecting CCD camera 113), 180 degrees (as for a fourth inspecting CCD camera 114), 220 degrees (as for a fifth inspecting CCD camera 115, a sixth inspecting CCD camera 116), 260 degrees (as for a seventh inspecting CCD camera 117), 305 degrees (as for an eighth inspecting CCD camera 118), 317 degrees (as for a ninth inspecting CCD camera 119), respectively.

Further, an angle of elevation of the optical axis of the first inspecting CCD camera 111 is 40 degrees, an angle of elevation of the optical axis of the second inspecting CCD camera 112 is 35 degrees, an angle of elevation of the optical axis of the third inspecting CCD camera 113 is 0 degrees, an angle of elevation of the optical axis of the fourth inspecting CCD camera 114 is 50 degrees, an angle of elevation of the optical axis of the fifth inspecting CCD camera 115 is 40 degrees, an angle of elevation of the optical axis of the sixth inspecting CCD camera 116 is 10 degrees, an angle of elevation of the optical axis of the seventh inspecting CCD camera 117 is 35 degrees, an angle of elevation of the optical axis of the eighth inspecting CCD camera 118 is 35 degrees, and an angle of elevation of the optical axis of the ninth inspecting CCD camera 119 is 0 degrees.

Figure 16:
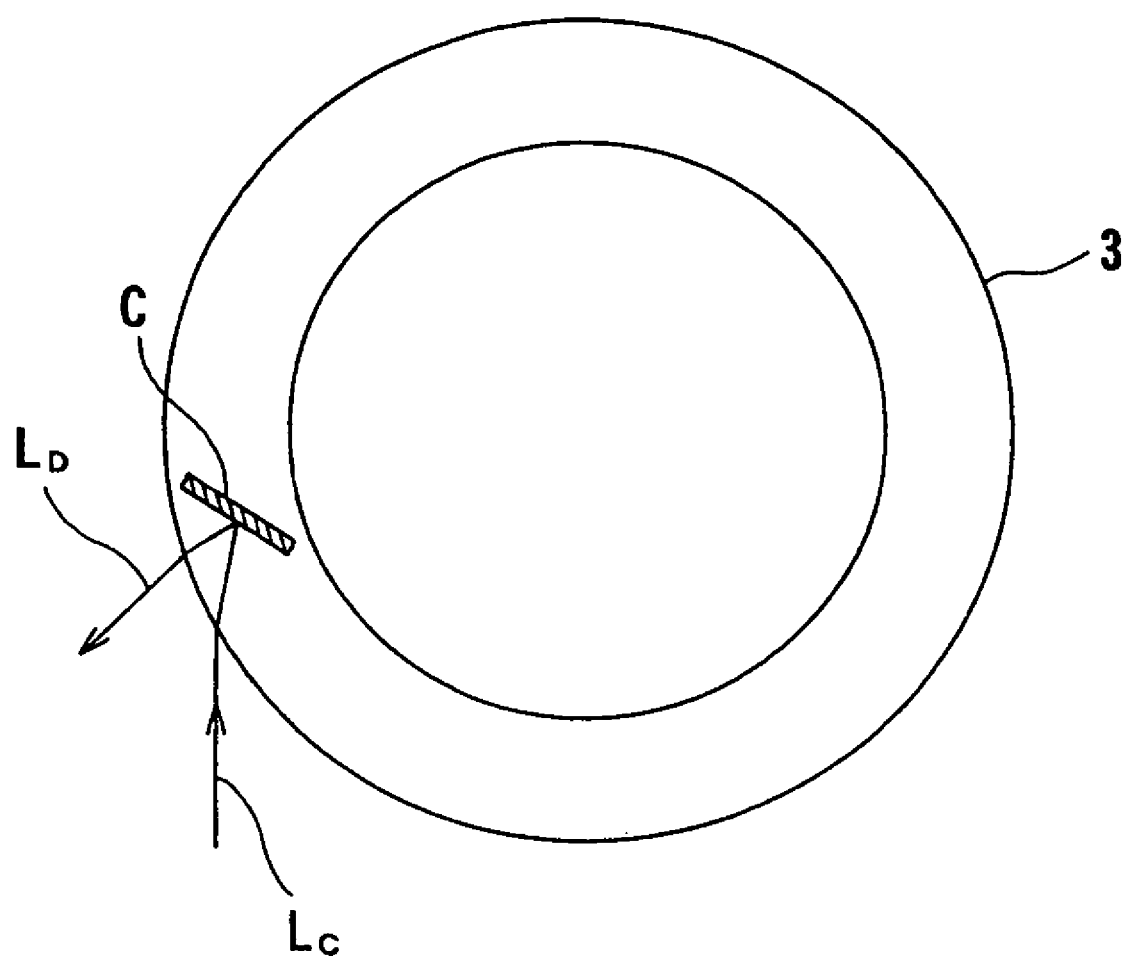
FIG. 16 is a schematic view showing the behavior of light from a lighting device according to the second embodiment of the present invention.

As shown in FIG. 16, light $L_C$ from the first lighting device 107a is incident into the bottle-mouth portion 3 from the outer circumferential surface of the bottle-mouth portion 3 of the glass bottle 2. If there is a check (vertical check) C inside the bottle-mouth portion 3, the light $L_C$ is reflected by the crack plane of the check C inside the bottle-mouth portion 3, and the reflected light $L_D$ passes through the bottle-mouth portion 3 and is imaged by the inspecting CCD cameras 111-119. The light $L_C$ reflected by the crack plane of the check C is brighter than light which has passed through other parts, and hence the part corresponding to the check C becomes a brighter area than other parts in the image which has been imaged by each of the CCD cameras. The image processor provided in the inspecting apparatus detects such a brighter area in the image obtained by each of the above CCD cameras 111-119 and judges this brighter area to be a check. On the other hand, if there is no check C inside the bottle-mouth portion 3, the light $L_C$ from the first lighting device 107a is incident into the bottle-mouth portion 3 from the outer circumferential surface of the bottle-mouth portion 3, and passes through the bottle-mouth portion 3 or is reflected from the outer circumferential surface of the bottle-mouth portion 3. In this case, if there is a molding failure in the screw thread portion or the like, the light from the molding failure part is scattered in directions where such light is not incident on the corresponding CCD cameras. Thus, the image becomes dimmer and blurrier than the image of the normally molded screw thread portion, and hence the molding failure can be detected. The structure of the image processor is the same as that of the image processor in the inspecting apparatus according to the first embodiment, and the description of the former is omitted.

Next, the operation of the glass bottle inspecting apparatus having the above structure will be described with reference to FIGS. 13 through 16.

Infrared light from the second lighting device 107b is applied to the bottle mouth from a side part of the bottle-mouth portion 3 of the glass bottle 2 placed on the turntable 1, and then passes through the bottle-mouth portion 3. The infrared light which has passed through the bottle-mouth portion 3 is imaged by the angle detection camera 110 provided so as to face the second lighting 107b. In the same manner as the first embodiment, the angle detection camera 110 images the thread screw on the bottle-mouth portion 3 to detect the rotation angle of the glass bottle with respect to the reference position at the time of imaging.

On the other hand, diffused light from the first lighting 107a is applied to the bottle-mouth portion 3 of the glass bottle 2 placed on the turntable 1. The inspecting CCD cameras 111-119 image light reflected from the bottle-mouth portion 3 of the glass bottle 2. In this case, if there is a check inside the bottle-mouth portion 3, the light which has been incident into the bottle-mouth from the outer circumferential surface of the bottle-mouth portion 3 is reflected by the crack plane of the check, and the reflected light passes through the bottle-mouth portion 3 and is imaged by the CCD cameras 111-119.

In a case where the angle detection camera 110 is taken as a reference, the relative positions of the respective inspecting CCD cameras 111-119 to the angle detection camera 110 are predetermined. Therefore, by displacing the reference position relatively, the rotation angle detected by the angle detection camera 110 can be used as a rotation angle when the respective inspecting CCD cameras 111-119 image the bottle-mouth portion 3. Therefore, in the present embodiment, the rotation angle which has been detected by the angle detection camera 110 is written on each of the images which have been imaged by the respective inspecting CCD cameras 111-119. As with the first embodiment, the image obtained from the glass bottle to be inspected is compared with the reference image (template) to judge the presence or absence of a check in the bottle-mouth portion.

As shown in FIG. 17, the computing boards 30-40 of the image processor 8 of the inspection apparatus in the first inspection station and the computing boards 130-139 of the image processor 108 of the inspection apparatus in the second inspection station are connected to a host computer 142 through, for example, an ethernet 141, thereby producing the above reference image. Specifically, images which have been imaged by the CCD cameras 10-20 and 110-119 in the respective inspection apparatuses may be sent to the host computer 142, and reference images may be produced by the host computer 142 on the basis of these images.

Although embodiments of the present invention have been described above, the present invention is not limited to the above embodiment, but various changes and modifications may be made therein within the scope of the technical concept.

As described above, according to the present invention, when light from the glass bottle is imaged while the glass bottle is illuminated and rotated, rotation angle information detected by the angle detection device can be written at a certain position on a corresponding image imaged by each of the CCD cameras. Therefore, according to the present invention, it is possible to recognize what the degree of imaging angle of the image imaged by each of the CCD cameras with respect to the reference position is.

Further, according to the present invention, the reference image is prepared in each angle in advance, and an actual image having angle information obtained by imaging the glass bottle to be inspected is compared with the reference image, and hence a defect at a specific part of the glass bottle can be detected. Therefore, if the reference image is prepared in each angle on the basis of the glass bottle having no defect (non-defective bottle), a defect at a specific part of the glass bottle can be detected by judging whether the actually obtained image in each angle has an area different from the reference image. Thus, when the type of glass bottle to be inspected is changed, it is not necessary to readjust the arrangement relationship between the lighting device serving as a light-emitting unit and the CCD camera serving as a light-receiving unit, and the adjustment time for changing the type of glass bottle can be remarkably shortened. Further, defects at a specific part of a glass bottle such as a check in a screw thread portion of the glass bottle, a check in a seam part of the bottle, and the like can be detected.

INDUSTRIAL APPLICABILITY

The present invention is suitable for use in a glass bottle inspecting apparatus which can detect a defect at a specific location of a bottle-mouth portion or the like of a glass bottle.

The invention claimed is:

1. An inspecting apparatus for detecting a defect of a glass bottle by imaging light from the glass bottle while the glass bottle is illuminated and rotated, and processing the obtained image, the inspecting apparatus comprising:
    a lighting device disposed at a predetermined position with respect to the glass bottle;
    a plurality of CCD cameras disposed around the glass bottle for imaging a specific part of the glass bottle;
    an angle detection device for visually detecting a rotation angle of the glass bottle with respect to a reference position rotation angle being obtained by imaging the glass bottle to be inspected; and
    an image processor for processing the images obtained by said CCD cameras;
    wherein said image processor stores rotation angle information detected by said angle detection device in such a manner that said rotation angle information corresponds to the image imaged by each of said CCD cameras.

2. An inspecting apparatus according to claim 1, wherein said rotation angle information is included on the image imaged by at least one of said CCD cameras.

3. An inspecting apparatus according to claim 1, wherein said image processor detects the defect at a specific part of the glass bottle by comparing the image having said rotation angle information with a reference image prepared in advance having corresponding rotation angle information.

4. An inspecting apparatus according to claim 3, wherein said reference image is produced in advance on the basis of images of glass bottles having no defect.

5. An inspecting apparatus according to claim 1, wherein mold information is stored in such a manner that said mold information corresponds to the image imaged by each of said CCD cameras.

6. An inspecting apparatus according to claim 1, wherein information related to production including manufacturing number, manufacturing line, or manufacturing date and time is stored in such a manner that said information corresponds to the image imaged by each of said CCD cameras.

7. An inspecting apparatus according to claim 1, wherein an inspection result is stored in such a manner that said inspection result corresponds to the image imaged by each of said CCD cameras.

8. An inspecting apparatus for detecting a defect of a glass bottle by imaging light from the glass bottle while the glass bottle is illuminated and rotated, and processing the obtained image, the inspecting apparatus comprising:
    a lighting device disposed at a predetermined position with respect to the glass bottle;
    a plurality of CCD cameras disposed around the glass bottle for imaging a specific part of the glass bottle;
    an angle detection device for visually detecting a rotation angle of the glass bottle with respect to a pre-determined reference position rotation angle being obtained by imaging the glass bottle to be inspected; and
    an image processor for processing the images obtained by said CCD cameras;
    wherein said image processor stores rotation angle information detected by said angle detection device in such a manner that said rotation angle information corresponds to the image imaged by each of said CCD cameras.

9. An inspecting apparatus for detecting a defect of a glass bottle by imaging light from the glass bottle while the glass bottle is illuminated and rotated, and processing the obtained image, the inspecting apparatus comprising:
   a lighting device disposed at a predetermined position with respect to the glass bottle;
   a plurality of CCD cameras disposed around the glass bottle for imaging a specific part of the glass bottle to detect the defect;
   an angle detection device for visually detecting a rotation angle of the glass bottle with respect to a reference position rotation angle being obtained by imaging the glass bottle to be inspected; and
   an image processor for processing the images obtained by said CCD cameras;
   wherein said image processor stores rotation angle information detected by said angle detection device in such a manner that said rotation angle information corresponds to the image imaged by each of said CCD cameras.

* * * * *